United States Patent
Stack et al.

(10) Patent No.: US 7,628,821 B2
(45) Date of Patent: *Dec. 8, 2009

(54) OBESITY TREATMENT METHOD

(75) Inventors: Richard S. Stack, Chapel Hill, NC (US); Fred E. Silverstein, Seattle, WA (US); Nathan Every, Seattle, WA (US); William L. Athas, Durham, NC (US); Michael S. Williams, Santa Rosa, CA (US); Richard A. Glenn, Chapel Hill, NC (US); John Lunsford, San Carlos, CA (US); Dan Balbierz, Redwood City, CA (US)

(73) Assignee: Barosense, Inc., Redwood City, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 11/195,204

(22) Filed: Aug. 2, 2005

(65) Prior Publication Data

US 2005/0267499 A1  Dec. 1, 2005

Related U.S. Application Data

(63) Continuation of application No. 10/387,031, filed on Mar. 12, 2003, now Pat. No. 7,146,984, which is a continuation-in-part of application No. 10/118,289, filed on Apr. 8, 2002, now Pat. No. 6,845,776.

(51) Int. Cl.
*A61B 19/00* (2006.01)
*A61F 2/04* (2006.01)

(52) U.S. Cl. ............. 623/23.64; 623/23.65; 128/898; 604/9

(58) Field of Classification Search ........... 623/23.64, 623/23.65, 23.67, 23.68, 23.7, 2.38, 2.4; 128/898

See application file for complete search history.

(56) References Cited

U.S. PATENT DOCUMENTS

| 1,408,865 | A | 3/1922 | Cowell |
| 3,663,965 | A | 5/1972 | Lee et al. |
| 4,246,893 | A | 1/1981 | Berson |
| 4,315,509 | A | 2/1982 | Smit |
| 4,403,604 | A | 9/1983 | Wilkinson et al. |

(Continued)

FOREIGN PATENT DOCUMENTS

CH    680263  A5    7/1992

(Continued)

OTHER PUBLICATIONS

In re PCT Patent Application No. PCT/US2004/006695, "Notification of Transmittal of the International Search Report," mailed Sep. 8, 2004, 7 pages in length.

(Continued)

*Primary Examiner*—Corrine M McDermott
*Assistant Examiner*—Megan Wolf
(74) *Attorney, Agent, or Firm*—King & Spalding LLP; Peter J. Dehlinger; Kathleen A. Frost

(57) ABSTRACT

A prosthetic device is described that is positionable within the gastro-esophageal junction region of a patient. The prosthetic device includes a proximal opening and a distal orifice that is adjustable in size prior to and/or following implantation. During use, the prosthetic device is attached to tissue of the gastro-esophageal junction region of the patient, with the device positioned such that food ingested by the patient passes from the esophagus through the proximal opening into the interior of the prosthetic device, and eventually exits the prosthetic device via the distal opening.

10 Claims, 10 Drawing Sheets

U.S. PATENT DOCUMENTS

| | | | |
|---|---|---|---|
| 4,416,267 A | 11/1983 | Garren et al. |
| 4,441,215 A | 4/1984 | Kaster |
| 4,467,804 A | 8/1984 | Hardy et al. |
| 4,501,264 A | 2/1985 | Rockey |
| 4,607,618 A | 8/1986 | Angelchik |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,899,747 A | 2/1990 | Garren et al. |
| 4,969,896 A | 11/1990 | Shors |
| 4,997,084 A | 3/1991 | Opie et al. |
| 5,037,021 A | 8/1991 | Mills et al. |
| 5,061,275 A | 10/1991 | Wallsten et al. |
| 5,088,979 A | 2/1992 | Filipi et al. |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shain |
| 5,401,241 A | 3/1995 | Delany |
| 5,403,326 A | 4/1995 | Harrison et al. |
| 5,405,377 A | 4/1995 | Cragg |
| 5,486,187 A | 1/1996 | Schneck |
| 5,514,176 A | 5/1996 | Bosley, Jr. |
| 5,571,116 A | 11/1996 | Bolanos et al. |
| 5,593,434 A | 1/1997 | Williams |
| 5,609,624 A | 3/1997 | Kalis |
| 5,628,786 A | 5/1997 | Banas et al. |
| 5,653,743 A | 8/1997 | Martin |
| 5,662,713 A | 9/1997 | Andersen et al. |
| 5,674,241 A | 10/1997 | Bley et al. |
| 5,709,657 A | 1/1998 | Zimmon |
| 5,720,776 A | 2/1998 | Chuter et al. |
| 5,749,918 A | 5/1998 | Hogendijk et al. |
| 5,771,903 A | 6/1998 | Jakobsson |
| 5,792,119 A | 8/1998 | Marx |
| 5,820,584 A | 10/1998 | Crabb |
| 5,839,639 A | 11/1998 | Sauer et al. |
| 5,848,964 A | 12/1998 | Samuels |
| 5,861,036 A | 1/1999 | Godin |
| 5,868,141 A | 2/1999 | Ellias |
| 5,887,594 A | 3/1999 | LoCicero, III |
| 5,897,562 A | 4/1999 | Bolanos et al. |
| 5,910,144 A | 6/1999 | Hayashi |
| 5,922,019 A | 7/1999 | Hankh et al. |
| 5,947,983 A | 9/1999 | Solar et al. |
| 5,993,483 A | 11/1999 | Gianotti |
| 6,016,848 A | 1/2000 | Egres, Jr. |
| 6,051,015 A | 4/2000 | Maahs |
| 6,086,600 A | 7/2000 | Kortenback |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli |
| 6,159,238 A | 12/2000 | Killion et al. |
| 6,197,022 B1 | 3/2001 | Baker |
| 6,206,930 B1 | 3/2001 | Burg et al. |
| 6,245,088 B1 | 6/2001 | Lowery |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,302,917 B1 | 10/2001 | Dua et al. |
| 6,358,197 B1 | 3/2002 | Silverman |
| 6,425,916 B1 | 7/2002 | Garrison et al. |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor et al. |
| 6,572,627 B2 | 6/2003 | Gabbay |
| 6,572,629 B2 | 6/2003 | Kalloo |
| 6,575,896 B2 | 6/2003 | Silverman |
| 6,592,596 B1 | 7/2003 | Geitz |
| 6,596,023 B1 | 7/2003 | Nunez et al. |
| 6,663,639 B1 | 12/2003 | Laufer et al. |
| 6,675,809 B2 | 1/2004 | Stack et al. |
| 6,740,121 B2 | 5/2004 | Geitz |
| 6,746,460 B2 | 6/2004 | Gannoe et al. ............ 606/153 |
| 6,764,518 B2 | 7/2004 | Godin |
| 6,773,440 B2 | 8/2004 | Gannoe et al. |
| 6,773,441 B1 | 8/2004 | Laufer et al. |
| 6,821,285 B2 | 11/2004 | Laufer et al. |
| 6,835,200 B2 | 12/2004 | Laufer et al. |
| 6,845,776 B2 | 1/2005 | Stack et al. |
| 6,981,978 B2 | 1/2006 | Gannoe |
| 6,994,715 B2 | 2/2006 | Gannoe et al. |
| 7,020,531 B1 | 3/2006 | Colliou et al. |
| 7,025,791 B2 | 4/2006 | Levine et al. |
| 7,037,344 B2 | 5/2006 | Kagan et al. |
| 7,097,650 B2 | 8/2006 | Weller et al. |
| 7,097,665 B2 | 8/2006 | Stack et al. |
| 7,146,984 B2 | 12/2006 | Stack et al. |
| 7,152,607 B2 | 12/2006 | Stack et al. |
| 7,175,638 B2 | 2/2007 | Gannoe et al. |
| 7,220,237 B2 | 5/2007 | Gannoe et al. |
| 7,335,210 B2 | 2/2008 | Smit |
| 7,354,454 B2 | 4/2008 | Stack et al. |
| 7,431,725 B2 | 10/2008 | Stack et al. |
| 2001/0011543 A1 | 8/2001 | Forsell ............ 128/899 |
| 2001/0020190 A1 | 9/2001 | Taylor |
| 2001/0021796 A1 | 9/2001 | Silverman et al. |
| 2002/0055757 A1 | 5/2002 | Torre et al. ............ 606/191 |
| 2002/0072761 A1 | 6/2002 | Abrams et al. |
| 2002/0082621 A1 | 6/2002 | Schurr et al. |
| 2002/0099439 A1 | 7/2002 | Schwartz et al. |
| 2003/0040808 A1 | 2/2003 | Stack et al. ............ 623/23.65 |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0120289 A1 | 6/2003 | McGuckin, Jr. et al. |
| 2003/0191476 A1 | 10/2003 | Smit ............ 606/108 |
| 2003/0208209 A1 | 11/2003 | Gambale et al. |
| 2004/0006351 A1 | 1/2004 | Gannoe et al. |
| 2004/0044353 A1 | 3/2004 | Gannoe ............ 606/153 |
| 2004/0044354 A1 | 3/2004 | Gannoe et al. |
| 2004/0044357 A1 | 3/2004 | Gannoe et al. ............ 606/194 |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0107004 A1 | 6/2004 | Levine et al. ............ 623/23.64 |
| 2004/0143342 A1 | 7/2004 | Stack et al. |
| 2004/0148034 A1 | 7/2004 | Kagan et al. |
| 2004/0162568 A1 | 8/2004 | Saadat et al. |
| 2004/0210243 A1 | 10/2004 | Gannoe et al. |
| 2004/0225183 A1 | 11/2004 | Michlitsch et al. |
| 2004/0225305 A1 | 11/2004 | Ewers et al. |
| 2005/0049718 A1 | 3/2005 | Dann et al. |
| 2005/0075654 A1 | 4/2005 | Kelleher |

| | | | |
|---|---|---|---|
| 2005/0085787 A1 | 4/2005 | Laufer et al. | |
| 2005/0096673 A1 | 5/2005 | Stack et al. | |
| 2005/0177181 A1 | 8/2005 | Kagan et al. | |
| 2005/0192599 A1 | 9/2005 | Demarais | |
| 2005/0251158 A1 | 11/2005 | Sadat et al. | |
| 2005/0251162 A1 | 11/2005 | Rothe et al. | |
| 2005/0256533 A1 | 11/2005 | Roth et al. | |
| 2006/0151568 A1 | 7/2006 | Weller et al. | |
| 2006/0178560 A1 | 8/2006 | Saadat et al. | |
| 2006/0195139 A1 | 8/2006 | Gertner | |
| 2006/0253142 A1 | 11/2006 | Bjerken | |
| 2006/0271076 A1 | 11/2006 | Weller et al. | |
| 2006/0282095 A1 | 12/2006 | Stokes et al. | |
| 2007/0032800 A1 | 2/2007 | Oritz et al. | |
| 2007/0043384 A1 | 2/2007 | Oritz et al. | |
| 2007/0055292 A1 | 3/2007 | Oritz et al. | |
| 2007/0175488 A1 | 8/2007 | Cox et al. | |
| 2007/0191870 A1 | 8/2007 | Baker et al. | |
| 2007/0191871 A1 | 8/2007 | Baker et al. | |
| 2007/0219571 A1 | 9/2007 | Balbierz et al. | |
| 2008/0190989 A1 | 8/2008 | Crews et al. | |
| 2008/0208355 A1 | 8/2008 | Stack et al. | |
| 2008/0294179 A1 | 11/2008 | Balbierz et al. | |
| 2009/0024143 A1 | 1/2009 | Crews et al. | |

FOREIGN PATENT DOCUMENTS

| | | |
|---|---|---|
| EP | 0 775 471 A1 | 5/1997 |
| EP | 1 602 336 A2 | 12/2005 |
| FR | 2768324 A1 | 3/1999 |
| WO | WO 91/01117 | 2/1991 |
| WO | WO 97/47231 A2 | 12/1997 |
| WO | WO 00/12027 | 3/2000 |
| WO | WO 00/32137 | 6/2000 |
| WO | WO 00/78227 A1 | 12/2000 |
| WO | WO 01/45485 | 6/2001 |
| WO | WO 01/49359 | 7/2001 |
| WO | WO 01/66018 A1 | 9/2001 |
| WO | WO 01/85034 A1 | 11/2001 |
| WO | WO 01/89393 A1 | 11/2001 |
| WO | WO 02/060328 A1 | 8/2002 |
| WO | WO 03/094784 | 11/2003 |
| WO | WO 03/099137 A2 | 12/2003 |
| WO | WO 2004/032760 A2 | 4/2004 |
| WO | WO 2004/110285 A1 | 12/2004 |
| WO | WO 2005/037152 A1 | 4/2005 |
| WO | WO 2005/079673 A2 | 9/2005 |
| WO | WO 2005/096991 A1 | 10/2005 |
| WO | WO 2006/016894 A1 | 2/2006 |
| WO | WO 2006/055365 A2 | 5/2006 |
| WO | WO 2007/041598 A1 | 4/2007 |

OTHER PUBLICATIONS

Cole et al., U.S. Appl. No. 12/050,169, filed Mar. 18, 2008, U.S. Appl. No. 12/050,169, 85 pages (2008).

Stecco, K. et al., "Trans-Oral Plication Formation and Gastric Implant Placement in a Canine Model", Stecco Group, San Jose and Barosnese, Inc., Redwood City, California (2004).

Stecco, K. et al., "Safety of A Gastric Restrictive Implant in a Canine Model", Stecco Group, San Jose and Barosnese, Inc., Redwood City, California (2004).

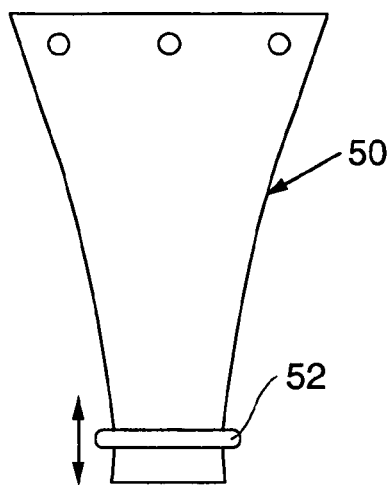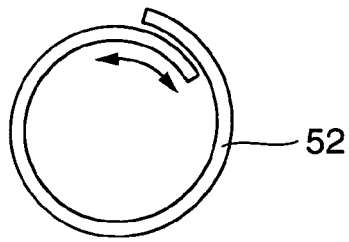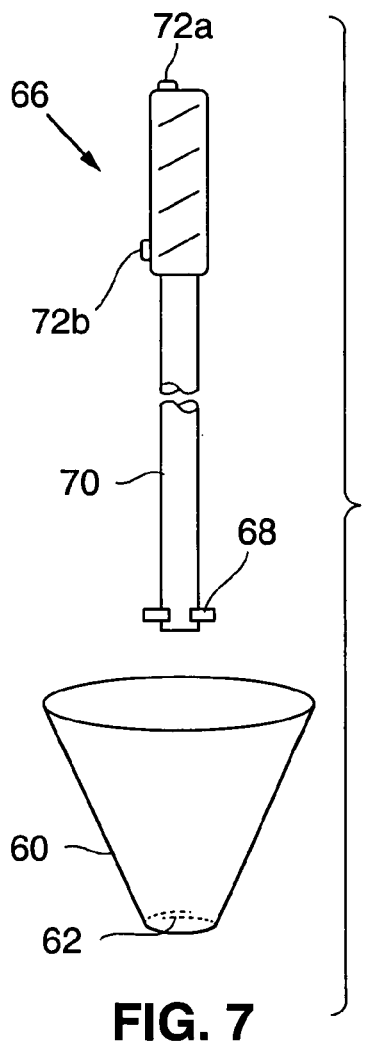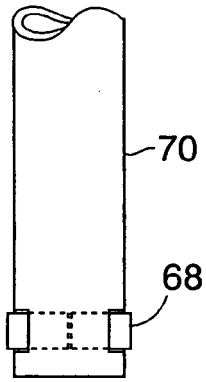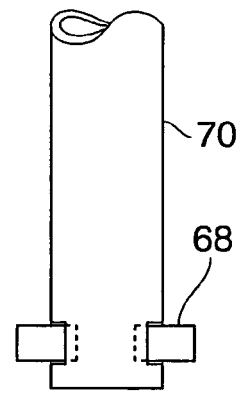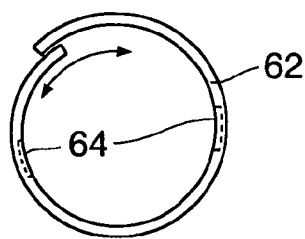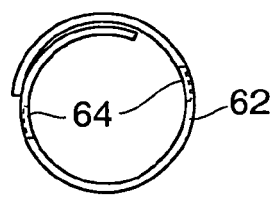

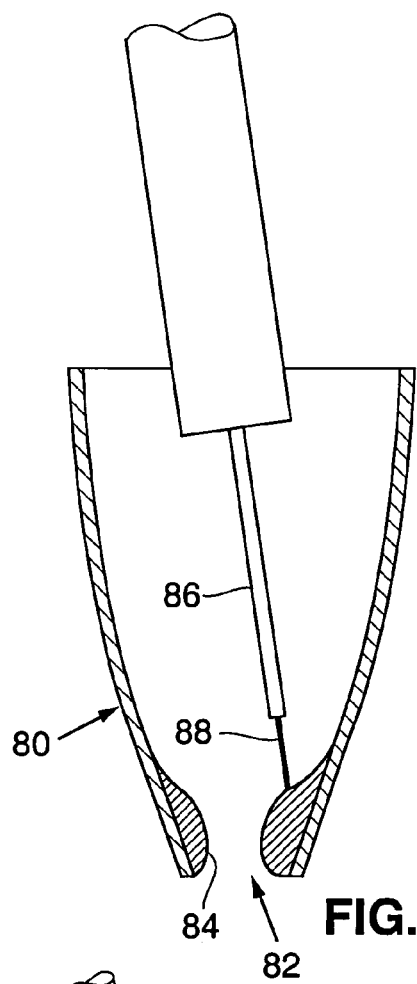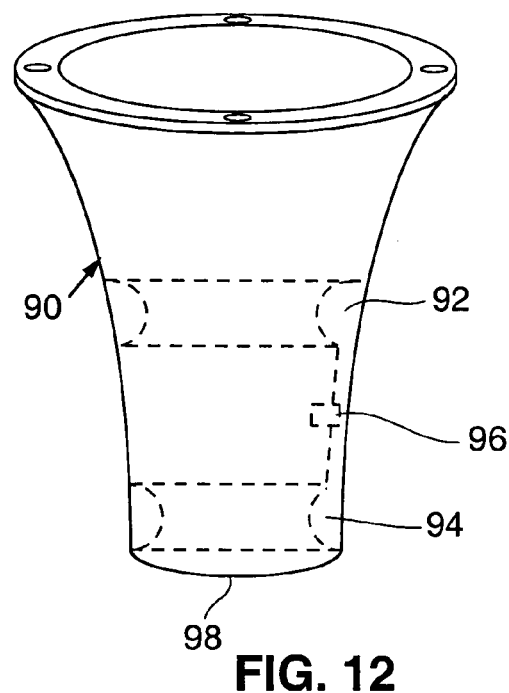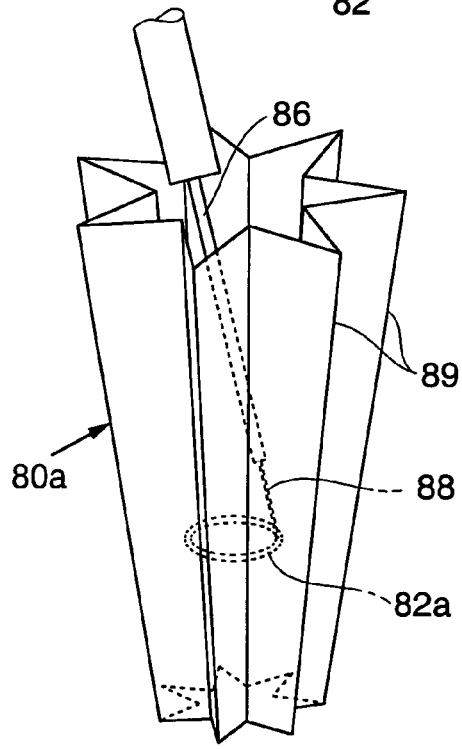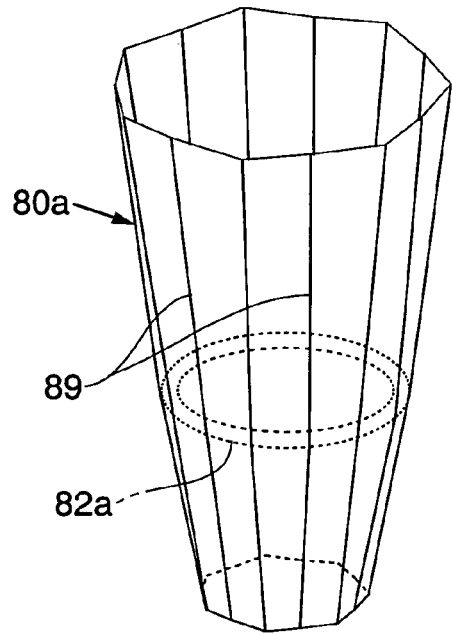
FIG. 10
FIG. 12
FIG. 11A
FIG. 11B

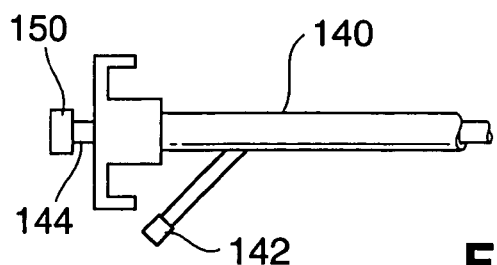
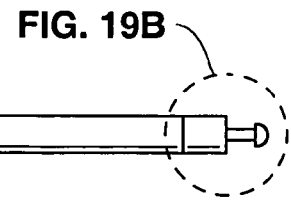
FIG. 19A
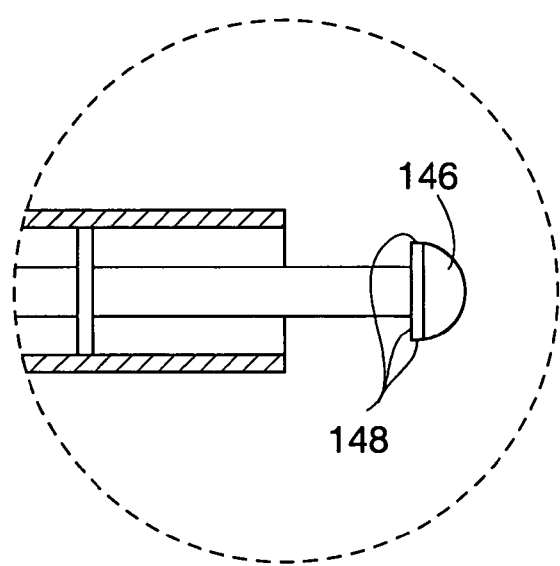
FIG. 19B
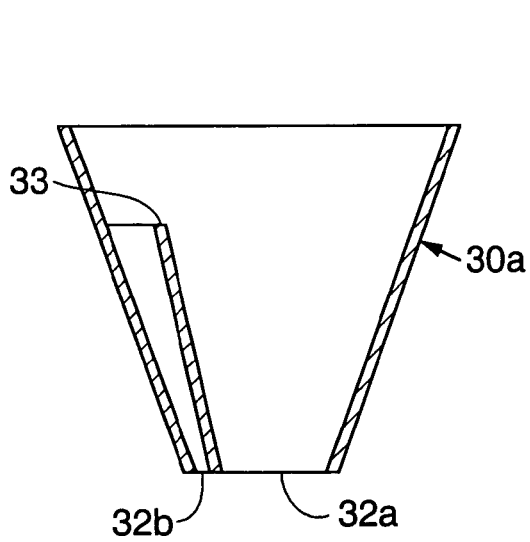
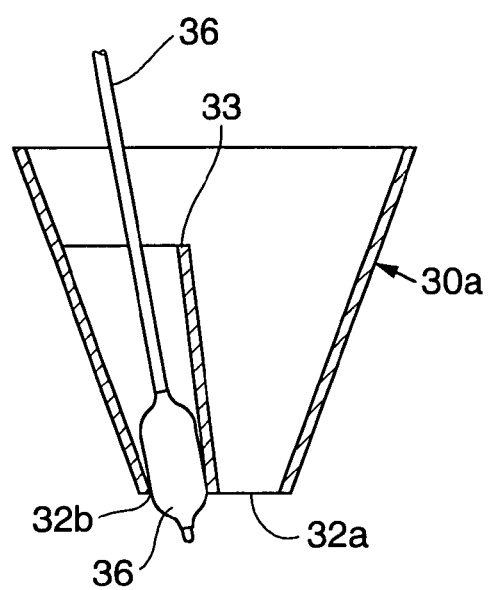
FIG. 20A  FIG. 20B

OBESITY TREATMENT METHOD

PRIORITY CLAIM

This application is a continuation of U.S. patent application Ser. No. 10/387,031, filed Mar. 12, 2003, now U.S. Pat. No. 7,146,984, which is a continuation-in-part of Ser. No. 10/118,289, filed Apr. 8, 2002, now U.S. Pat. No. 6,845,776.

FIELD OF THE INVENTION

The present invention relates generally to the field of devices and methods for achieving weight loss in humans, and specifically to the use of devices implantable within the human stomach for controlling feelings of hunger and/or limiting food intake.

BACKGROUND OF THE INVENTION

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Prosthetic devices for use in controlling obesity are shown and described in U.S. application Ser. No. 09/940,110, filed Aug. 27, 2001 and U.S. application Ser. No. 10/118,289 filed Apr. 8, 2002, and U.S. Provisional Application No. 60/379,306 filed May 10, 2002. These applications are owned by the assignee of the present application, and the disclosures of these applications are incorporated herein by reference. Certain forms of these devices involve positioning a prosthetic pouch in the proximal stomach as shown in FIG. 1B. The pouch 2 includes a proximal opening 4 and a smaller distal opening 6 and forms a small reservoir that collects masticated food from the esophagus—thereby limiting the amount of food that can be consumed at one time. As the pouch fills with food, it may distend, imparting pressure against the upper stomach and lower esophageal sphincter causing the patient to experience sensations of fullness. The pouch may additionally or alternatively act as a restrictor, limiting the amount of food intake. The pouch is fixed in place using clips, sutures, suitable adhesives or other means 8 at anchor points around the perimeter of the proximal opening 4.

The amount by which food intake should be restricted varies between patients. It may thus be desirable to increase or decrease the amount of food a patient can ingest by selecting an appropriate diameter for the pouch's distal orifice. A smaller orifice will cause food to descend from the pouch into the stomach more slowly than will a larger orifice, and will thus limit the amount of food the patient can consume at one time.

Satiation pouches may be available in multiple distal orifice sizes (and/or multiple pouch sizes) to permit the physician to select a size that is appropriate for the targeted food intake for the patient. Alternatively, satiation pouches may be configured to allow the size of the pouch's distal opening to be increased or decreased. This enables a physician implanting such a device to set the distal opening to a size appropriate for a patient. In some cases, it will also allow the physician to make adjustments to the distal opening after it has been implanted. For example, if the patient is not losing weight at a desired rate, the physician might reduce the size of the distal opening—so that food will empty more slowly from the pouch into the stomach. The physician might alternatively increase the size of the distal opening if necessary if weight loss is occurring too rapidly—or if the patient is suffering from nausea and requires that the pouch be opened to allow the patient to vomit more easily. The present application describes various satiation pouches which have adjustable distal orifice sizes and which thereby provide the physician with enhanced control over the degree of food consumed by the patient at one time.

SUMMARY OF THE INVENTION

The present invention includes a prosthetic device positionable within the gastro-esophageal junction region of a patient, wherein the prosthetic device includes a proximal opening and a distal orifice that is adjustable in size prior to and/or following implantation. During use, the prosthetic device is attached to tissue of the gastro-esophageal junction region of the patient, with the device positioned such that food ingested by the patient passes from the esophagus through the proximal opening into the interior of the prosthetic device, and eventually exits the prosthetic device via the distal opening.

BRIEF DESCRIPTION OF THE DRAWINGS

FIG. 6A is a front elevation view of a fifth embodiment of satiation pouch having an alternative form of adjustable distal opening.

FIG. 6B is a top plan view of the adjustable restrictor ring of the pouch of FIG. 6A.

FIG. 7 is a side elevation view of a sixth embodiment of a satiation pouch having yet another form of adjustable distal opening, and a tool useable for adjusting the distal opening.

FIGS. 8A and 8B are side elevation views showing the distal end of the tool shown in FIG. 7 in the retracted and expanding positions, respectively.

FIGS. 9A and 9B are top plan views of the adjustable restrictor ring of the pouch of FIG. 33, showing the ring in expanded and contracted positions.

FIG. 10 is a perspective view of a seventh embodiment of a satiation device together with a tool used to vary the diameter of the distal orifice.

FIGS. 11A and 11B are perspective views of a seventh embodiment of a satiation device together with a tool used to vary the diameter of the distal orifice.

FIG. 12 is a perspective view of a ninth embodiment of a satiation device.

FIG. 15B shows the pouch following reduction of the size of the distal orifice.

FIG. 19A is a side elevation view of a cutting tool for expanding the distal orifice size of a satiation pouch. FIG. 19B is a detailed view of the region within the circle 19B-19B in FIG. 19A.

FIG. 20A is a cross-sectional side perspective view of a satiation pouch having an adjustable orifice size.

FIG. 20B is a partially cutaway side perspective view of the pouch of FIG. 20A illustrating adjustment of the orifice size.

DETAILED DESCRIPTION OF THE DRAWINGS

Figure 1A:
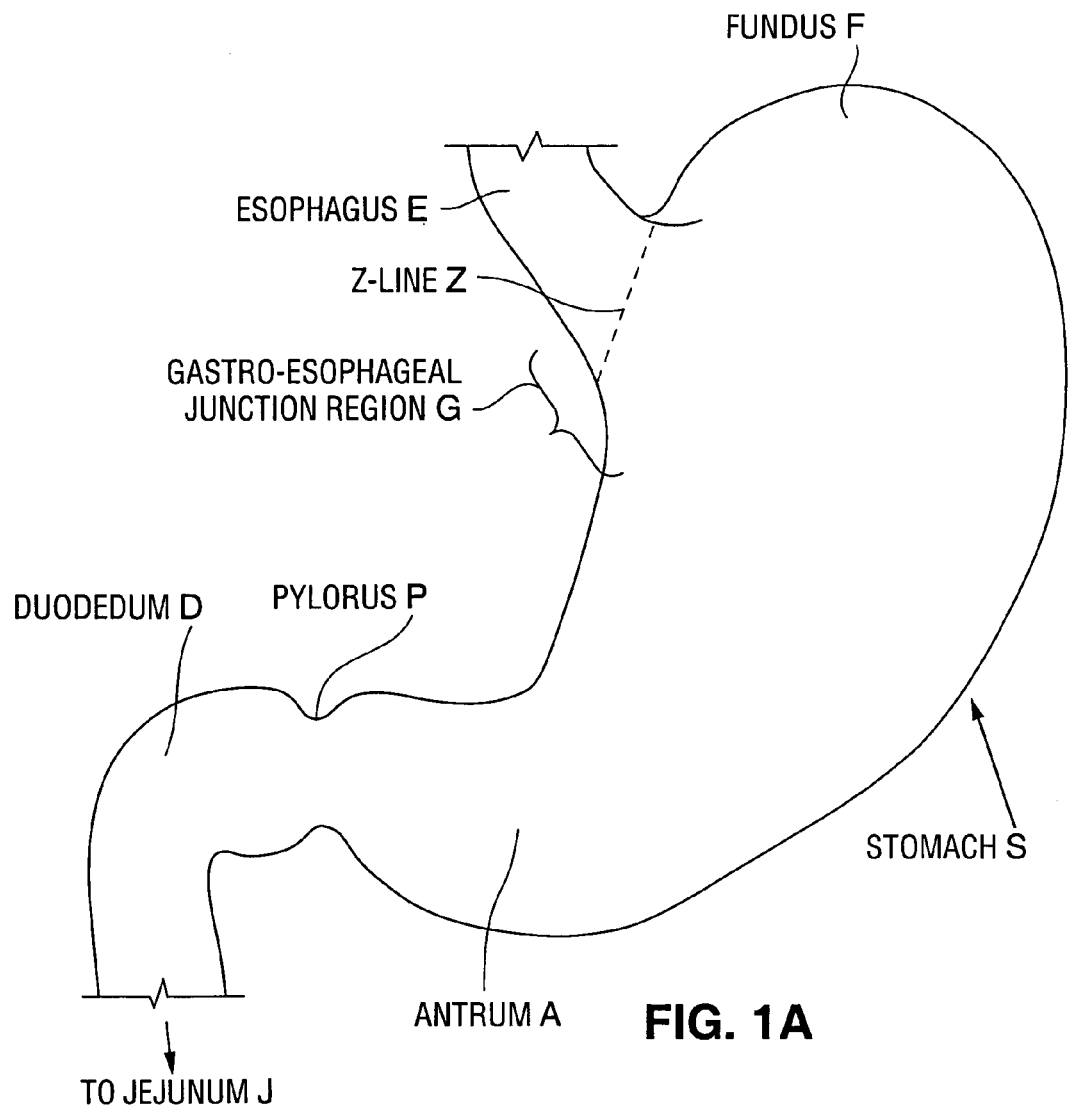
FIG. 1A is a schematic illustration of a human stomach and a portion of the small intestine.

The drawings show a number of embodiments of satiation pouches having features that permit the size of the distal or exit orifice to be altered before and/or following implantation. The term "exit orifice" will be used to describe the smallest orifice through which food flows from the interior of the pouch towards the stomach. In referring to the step of modifying the size of the distal orifice or exit orifice of the device, the term "size" will be used to refer to the dimensions that, when modified, will change the rate at which ingested food flows through the orifice.

For the purposes of this application, the term "satiation devices" or "satiation pouches" will be used to mean prosthetic devices including pouches intended to induce weight loss in one or more of a variety of ways. These include, but are not limited to, physically restricting the amount of food that can be consumed, and/or imparting pressure against portions of the body (e.g. stomach, esophagus, esophageal sphincter, etc) causing the patient to experience sensations of fullness, and/or affecting levels of hormones or other substances in the body that control or affect feelings of hunger, and/or affecting the amount of ingested food absorbed by the body.

The pouch of each described embodiment may be formed of a flexible material that will prevent passage of food through the sides of the pouch. Examples of such materials include, but are not limited to polyesters (e.g. Dacron® polyester), ePTFE fabric (e.g. GoreTex® fabric or others), a polyurethane such as ChronoFlex® polyurethane, nylon fabrics, silicone, other polymeric materials, and bio-absorbable materials (e.g. PLLA, PGA, PCL, poly-amhydride etc). The material may be a composite of compliant, semi-compliant and/or non-compliant materials that give different regions of the pouch different degrees of compliance so as to allow/limit expansion of the pouch in various locations. For example, it may be desirable to provide the pouch with a fairly elastic exit port to as to prevent occlusion in the event a large piece of food is ingested and/or to control the exit pressure of food from the pouch, whereas the proximal end of the pouch may be stiffer to prevent bulging. Varying degrees of compliance may also be built into the pouch by varying the cross-sectional thickness in different regions of the pouch. The material may be coated with a lubricious, bio-compatible, chemically inert material, such as paraleyne, to reduce friction on the base material's surface which will help prevent sticking and food build up on the device. The flexible pouch material may be reinforced with, constructed of, or supported by supporting members, such as a soft mesh, a cage structure, ribs, rings etc. The supporting members may be formed of stainless steel, polymer, shape memory materials such as nitinol, shape memory alloys, or shape memory polymers, or thickened regions of material. The pouch may be constructed so as to be self-expanding, such that the pouch springs radially open into an expanded condition upon ejection from a deployment device or catheter.

Implantation of the described devices is preferably performed endoscopically, by passing the devices through the esophagus, preferably under endoscopic visualization. Alternatively, the devices may be implanted using surgical or laparoscopic procedures.

During implantation the pouch is secured at the gastroesophageal junction region G using sutures, clips, adhesives, stents or stent-like structures, or other suitable means. One suture attachment device found useful for applying sutures between the pouch and tissue is the "Sew-Right" suturing device available from LSI Solutions of Victor, N.Y. Although the pouch may be secured to the esophageal tissue, it is more preferable to apply sutures/clips below the Z-line to allow for attachment to the thicker tissue of the stomach wall.

Figure 1B:
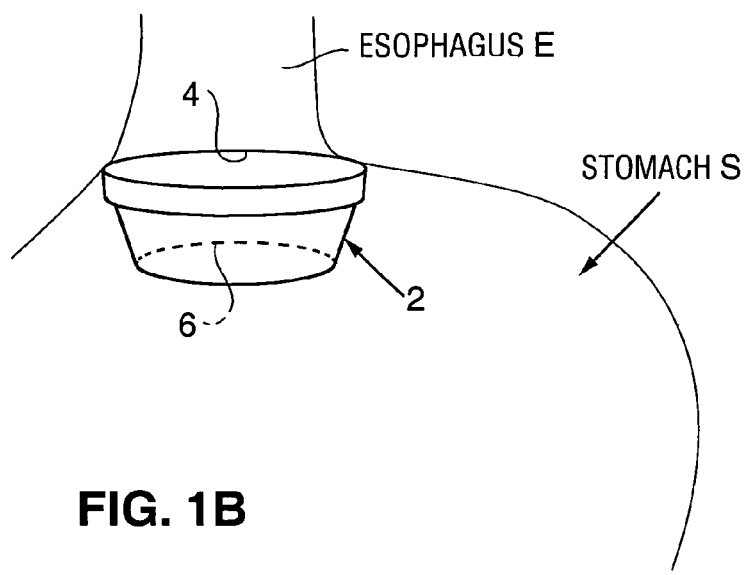
FIG. 1B is a perspective view of a satiation pouch shown positioned in the stomach.
Figure 2A:
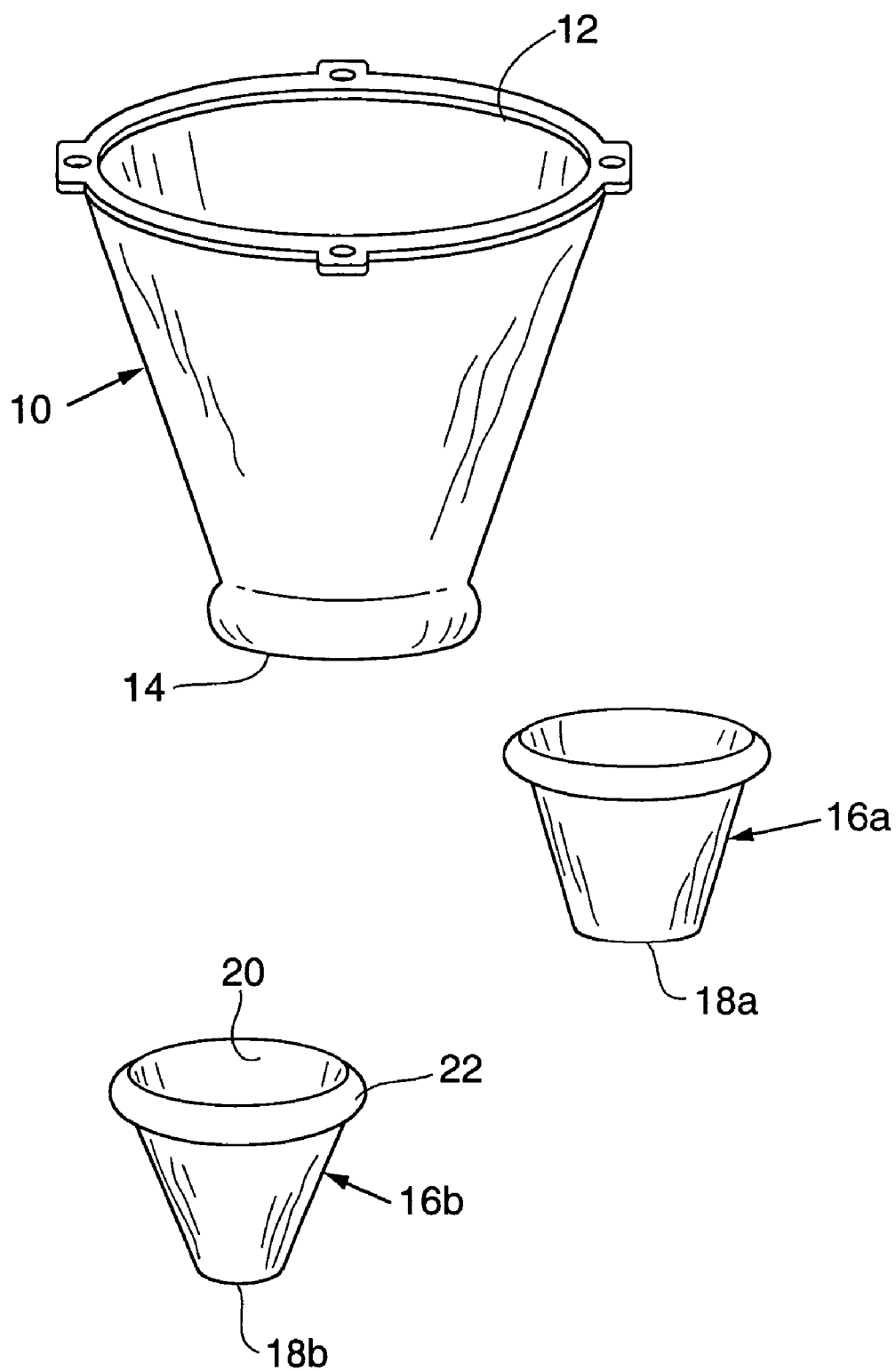
FIG. 2A is a perspective view of a first embodiment of a satiation pouch including a set of distal inserts each having a different distal orifice size.
Figure 2B:
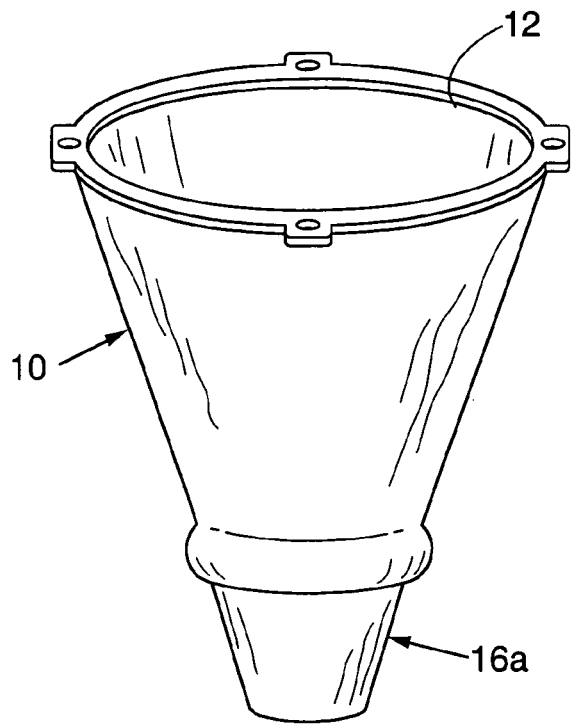
FIG. 2B is a perspective view of the satiation pouch of FIG. 2A having one of the distal inserts connected to the pouch.

Each of the described pouches includes a proximal opening and a distal exit port (see openings 4 and 6, respectively, of FIG. 1B). Because of its small volume (which may be on the order of approximately 2 cc-300 cc in volume, but is preferably in the range of 10-30 cc), the pouch functions to limit the amount of food that can be consumed at one time. Over time the food within this reservoir descends into the stomach through the exit port.

First Embodiment

A first embodiment of a satiation pouch having a variable-size orifice is shown in FIGS. 2A through 3C. Pouch 10 includes a proximal opening 12, a distal opening 14, and a passage extending between the proximal and distal openings. Inserts 16a, 16b are provided for attachment to the pouch 10. Preferably two or more such inserts 16a, 16b are provided, each with a different sized distal orifice 18a, 18b. For example, a collection of inserts may be provided with distal orifices each having different diameters in the range of 6-14 mm (for a circular orifice). Each insert includes a proximal opening 20 surrounded by a rim 22. Rim 22 is proportioned to seat within a recess 24 (FIG. 3A) formed in the interior wall of the pouch 10 when the insert 16a is placed inside the pouch with the orifice 18a extending in a distal direction. See FIGS. 2B and 3C. The rim 22 may be structurally reinforced using a ring formed of nitinol, stainless steel, thick silicone, etc if necessary to insure a snug fit between the insert and pouch.

Prior to implantation of the pouch 10, the physician selects an insert having a diameter that is appropriate for the patient. S/he does so by choosing an insert having a distal orifice size that will cause food to descend from the stomach at a desired rate. Next, the physician passes the insert through the proximal opening 12 of the pouch 10 and presses rim 22 of the insert into engagement with recess 24 of pouch. It may be necessary to dilate the distal opening 14 of the pouch while rim 22 is being seated within the recess 24.

Figure 3A:
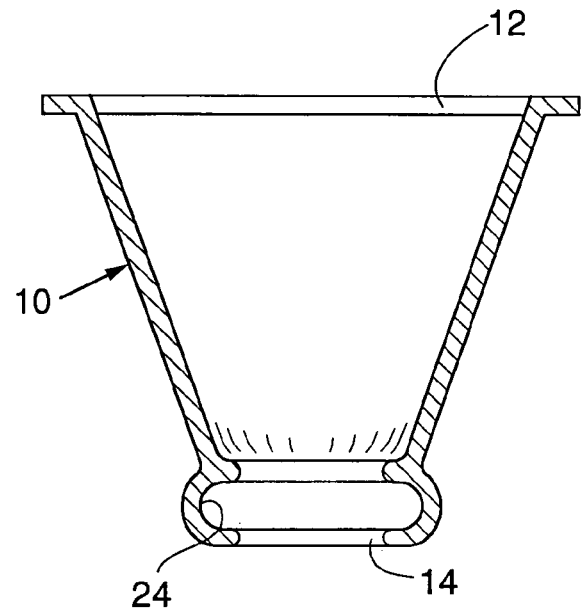
FIG. 3A is a cross-sectional side view of the pouch of FIG. 2A.
Figure 3B:
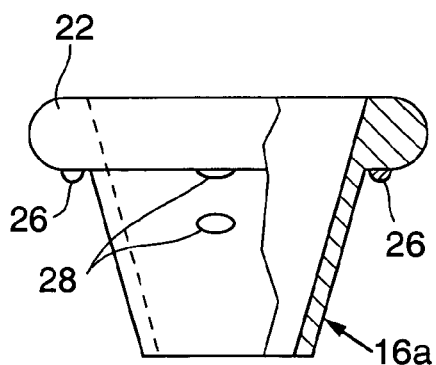
FIG. 3B is a cross-sectional side view of one of the distal inserts of FIG. 2A.
Figure 3C:
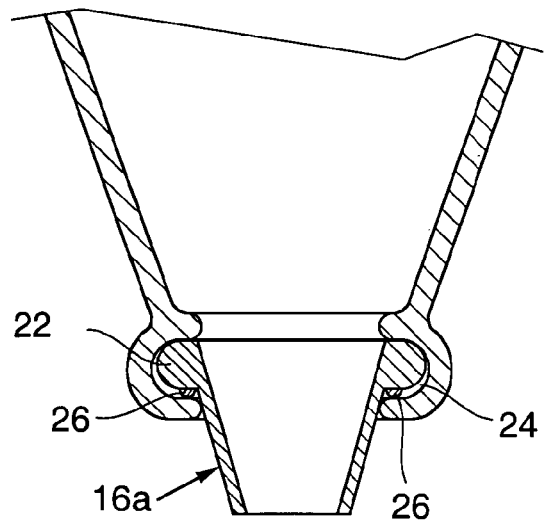
FIG. 3C is a cross-sectional side view of the distal portion of the pouch of FIG. 3A, with the insert of FIG. 3B assembled with the pouch.

The distal face of rim 22 may include bumps 26 as shown in FIG. 3B. When the pouch and insert are assembled, these bumps 26 urge the proximal face of the rim against the upper surface of the recess (FIG. 3C), so as to prevent accumulation of ingested food in spaces that would otherwise be left between them. The connection between the pouch and insert may be reinforced if desired using sutures or other means. After the pouch and insert are assembled, the pouch is implanted at the gastro-esophageal junction region.

It should be noted that assembly of the pouch and insert may alternatively be carried out after the pouch has been implanted. Holes 28 (FIG. 3B) facilitate grasping of the insert using forceps or other tools during assembly.

If the physician determines at a later time (for example, after hours, days, weeks, months or even years) that an insert having a different orifice size would be more appropriate for the particular stage of the patient's treatment, the insert 16a may be removed from the pouch 10 (such as by grasping it using forceps and withdrawing it through the proximal opening 12) and replaced with another pouch.

Although the pouch 10 is shown as having proximal opening 12 that is larger than the distal opening 14, the pouch may be provided with a larger distal opening 14, including one that is equal to or greater in size than the proximal opening. Such an embodiment might be used, for example, in a patient for whom it would be desirable to allow the patient to heal from the initial implantation and/or adjust to the presence of the implanted pouch before the exit orifice is reduced. After an appropriate healing/adjustment period (for example, at least one day and as long as approximately two weeks in order to allow the suture/anchor attachment points to heal), a separate procedure would be performed to add the insert or other flow restrictive component to the pouch 10, preferably by passing the component down the esophagus towards the stomach. During implantation of the insert or other component, it may be desirable to clear the pouch of any food material that may have accumulated in the recess 24. It should also be noted that if a healing/adjustment period is intended, the pouch design might be modified slightly so as to minimize the chance that food material will accumulate within the recess 24.

Another variation on the concept of adding a flow restrictive component after an initial adjustment period involves initially implanting a base device at the gastro-esophageal junction region, where the base device need not be a satiation pouch but is a base to which a pouch will be attached following the healing/adjustment period. For example, the base may take the form of an annular ring or other device that is secured at the gastro-esophageal junction region using sutures, clips, staples etc. The ring may be formed of a variety of materials, including those listed for use to form the pouch. After the healing/adjustment period, a satiation pouch may then be attached to the base using screws, snaps, sutures, clips, staples or other fasteners.

Many variations of the first embodiment are possible and are considered within the scope of applicant's disclosure. For example, the inserts may be replaced with other types of interchangeable components that add a larger or smaller orifice to the pouch. For example, one such component may be similar to the inserts 16a, 16b but attach to the exterior of the pouch rather than being seated in the pouch interior. Also, the inserts or alternative components may be attachable to the pouch using other means such as sutures, clips, adhesives, etc.

Second Embodiment

Figure 4A:
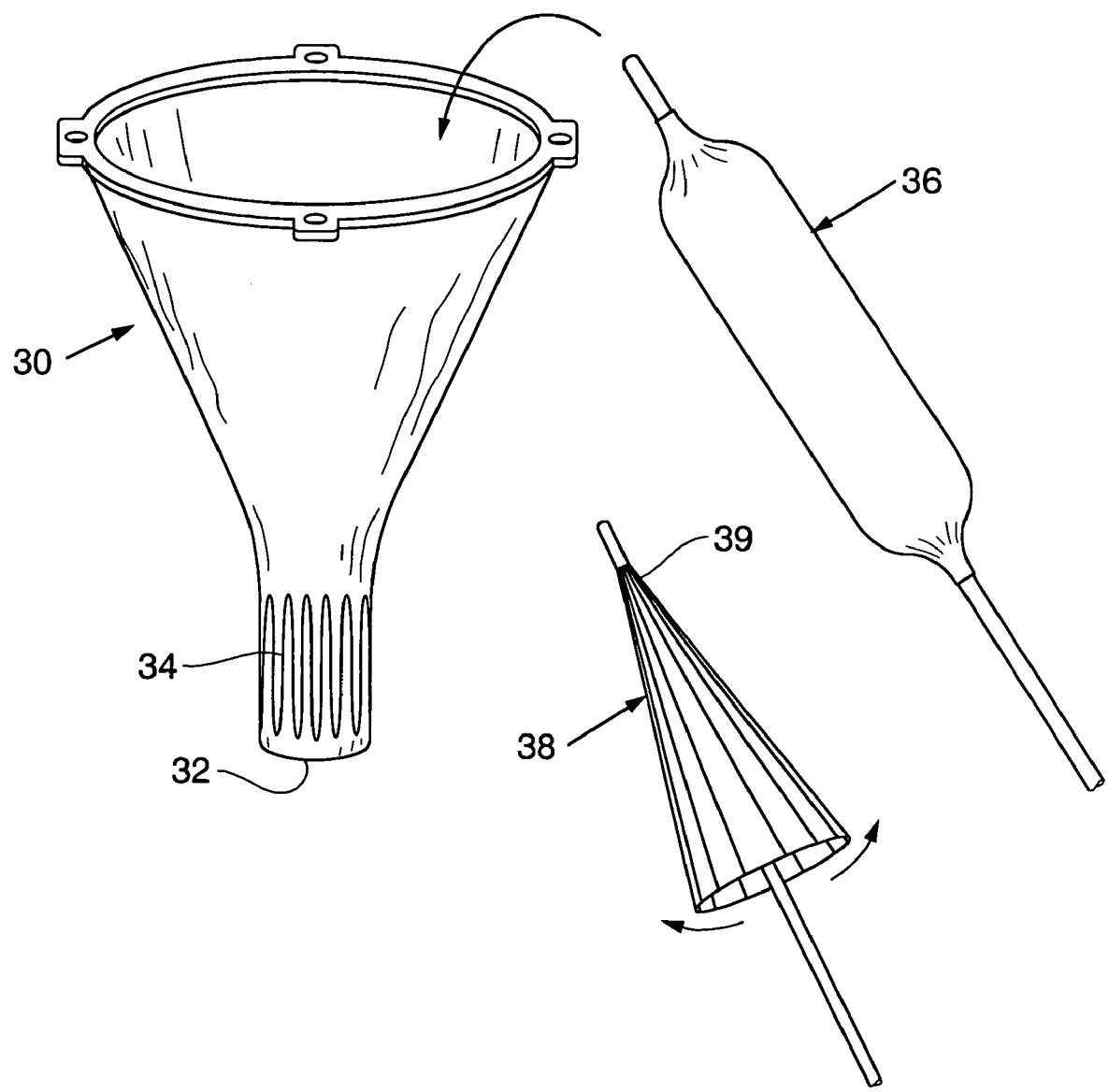
FIG. 4A is a perspective view of a second embodiment of a satiation pouch, shown together with devices for increasing and reducing the orifice diameter.

FIG. 4A shows a second embodiment of a satiation pouch 30. Pouch 30 includes a distal orifice 32 having a size that may be increased or decreased prior to or following implantation. A ductile ring 34 is located at the distal portion of the pouch, near the distal orifice 32. The ring is preferably formed of a malleable, ductile material (e.g. annealed stainless steel, copper or other metal, or plastic). It may be shaped in a spring configuration as shown, or it may have a stent-like or other type of configuration. Ring 34 may be on the interior or exterior surface of the pouch 30, or embedded within the pouch material.

Figure 4B:
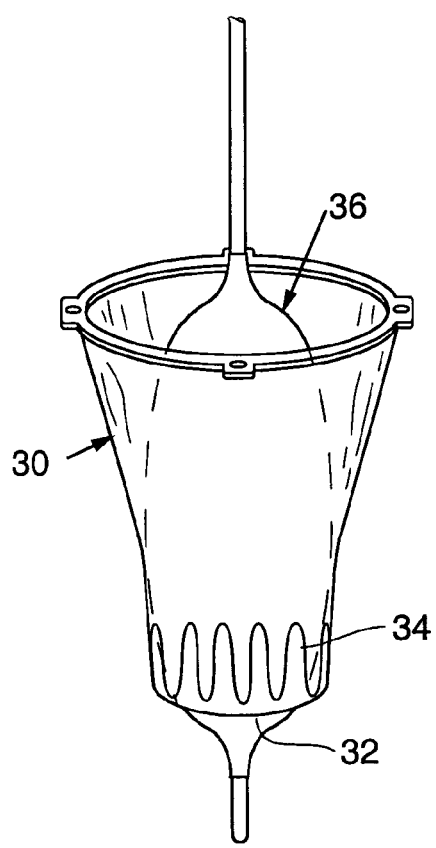
FIG. 4B is a perspective view of the pouch of FIG. 4A showing the expander in use to increase the orifice size.
Figure 4C:
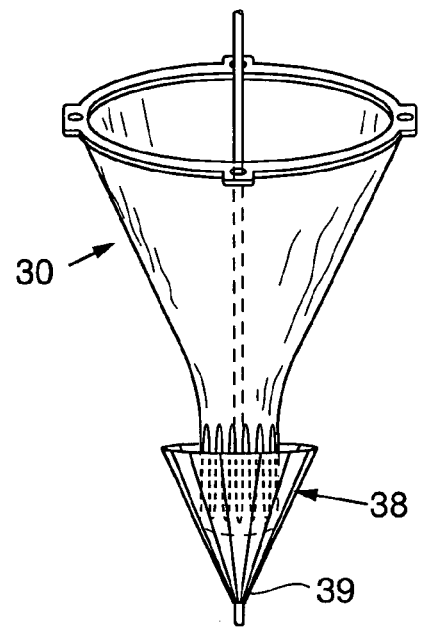
FIG. 4C is a perspective view of the pouch of FIG. 4A showing a reduction tool in use to decrease the orifice size.

Pouch 30 is provided with tools for use in increasing and decreasing the diameter of the ring 34 so as to increase/decrease the size of the distal orifice 32. For example, an expansion tool make take the form of a balloon dilator 36 positionable within the pouch and then inflated as shown in FIG. 4B to expand the ring 34. Another example might be an expandable basket-type catheter. A reduction tool 38 may have an umbrella-like configuration as shown in FIG. 4A. During use, the operative head 39 of the tool 38 is placed in its closed position and passed through the pouch and out the distal orifice 32. Once outside the distal orifice, the head 39 is expanded, drawn in a proximal direction such that it surrounds the ring 34 (FIG. 4C), and then moved to the closed position to press the ring into a smaller-diameter configuration. Afterwards, the tool 38 is withdrawn from the pouch.

In this and all of the described embodiments, modifications to the exit orifice size may be performed at various different stages in the patient's treatment. For example, if a physician determines following implantation of the pouch (for example, after hours, days, weeks, months or even years) that a prosthesis having a different orifice size would be more appropriate for the particular stage of the patient's treatment, the necessary tools may be passed through the esophagus and used to modify the orifice size. As another example, the pouch may be initially implanted with a large (e.g. as large as, or larger than, the proximal opening) exit orifice. Then, following an adjustment period and/or healing of the sutures/fasteners etc. at the implant site, a second procedure is performed to modify the exit orifice to a desired size.

FIGS. 20A and 20B illustrate another pouch in which malleable material may be used to provide adjustability to the exit orifice. Pouch 30a is provided with an exit orifice 32a and an adjustment orifice 32b, which share a common wall 33. The pouch 30a is constructed such that expansion of an expansion tool (e.g. balloon dilator 36) within adjustment orifice 32b reduces the size of exit orifice 32a, such as by deforming common wall 33 towards the exit orifice 32a as shown in FIG. 20B. Likewise, use of the expansion tool within exit orifice 32a will deform common wall 33 away from the exit orifice to increase the size of the exit orifice. A portion of the pouch, such as the wall 33 or rings/bands surrounding the distal and adjustment orifices, is preferably formed of a malleable material to allow the exit orifice 32*a* to retain it's adjusted size unless its size is further altered using the expansion tool.

Third and Fourth Embodiments

Figure 5A:
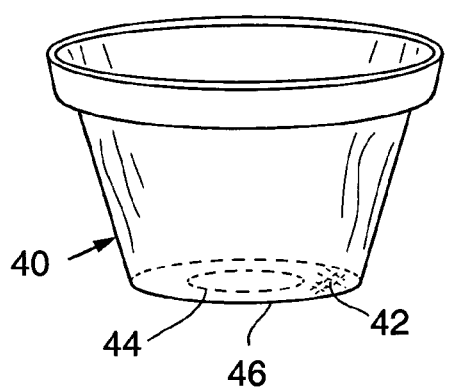
FIG. 5A is a perspective view of a third embodiment of a satiation device.

A variation on the second embodiment is the third embodiment shown in FIG. 5A. The third embodiment includes a pouch 40 having an annular web 42 at its distal end, forming a distal orifice 44. Examples of suitable materials for the webbing 42 include those listed above for use with the pouch. A low yield-strength ring 46 is connected to the exterior perimeter of the webbing. To increase the diameter of the orifice 44, a dilation tool such as dilator 36 of FIG. 4A is passed through the orifice 44 and expanded to expand the ring. The expanded ring draws the webbing radially outwardly, thereby increasing the size of the orifice 44. A reduction tool such as tool 38 of FIG. 4A may be used to compress the ring to a smaller-diameter size and to thereby reduce the diameter of the orifice 44.

Figure 5B:
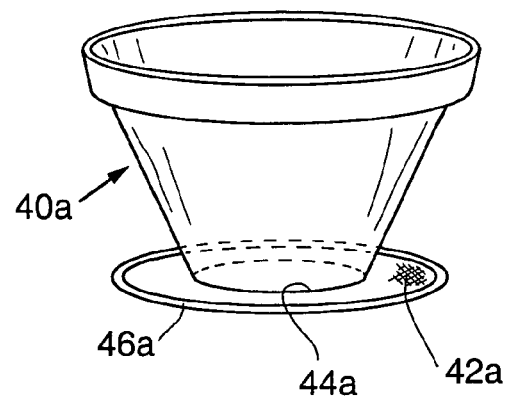
FIG. 5B is a perspective view of a fourth embodiment of a satiation device.

The pouch 40*a* of the fourth embodiment, shown in FIG. 5B, operates in similar fashion to that of the third embodiment, but includes webbing 42*a* and a ring 46*a* that extend radially outwardly from the distal orifice 44*a*.

Fifth and Sixth Embodiments

Referring to FIGS. 6A and 6B, a fifth embodiment of a pouch 50 may alternatively be provided with a restrictor ring 52 surrounding the exterior of the pouch—near the distal opening. Ring 52 may be expanded by applying expansive radial forces from within the inner diameter of the ring (e.g. using a dilator as described or by positioning the jaws of a grasper within the funnel and then separating the jaws), or compressed using compressive forces applied to the exterior of the ring (e.g. by positioning the ring between the jaws and then closing them slightly). This expansion/compression may be performed prior to implantation, or after the pouch has been implanted.

FIG. 7 shows a third alternative embodiment of a pouch 60 having an adjustable distal opening. The FIG. 7 embodiment is similar to the FIG. 6A embodiment in that it relies upon expansion/contraction of a restrictor ring 62. Restrictor ring 62 is positioned inside the pouch near the distal opening. A pair of opposed slots 64 are formed in the interior surface of the ring 62. An endoscopically-controllable adjustment tool 66 includes a pair of extendable pins 68 at the distal end of an elongate shaft 70. Actuators 72*a,b* on the proximal end of the adjustment tool 66 control extension of the pins between the retracted position (FIG. 8A) and the extended position (FIG. 8B). To adjust the diameter of the pouch 60, tool is inserted through the pouch with the pins 68 in the retracted position. Pins 68 are aligned with slots 64 in the ring 62 and are then extended using actuator 72*a*. As they extend, the pins 68 slide into the slots 64. Next, the user rotates the tool 70 about its longitudinal axis, in either the clockwise or counter-clockwise direction. Rotation of the tool expands or contracts the ring, depending on the direction of rotation. After the ring size has been adjusted, the pins 68 are retracted using actuator 72*b*, and the tool 66 is removed from the pouch 62.

Seventh Through Ninth Embodiments

An inflation medium such as gas or saline may be used to affect an increase or decrease in the distal orifice size, either before or after the pouch has been implanted. For example, in the seventh embodiment shown in FIG. 10, pouch 80 includes an inflatable annular region 82 adjacent to the distal orifice 84. An endoscopic inflation/deflation tool 86 is passed through the oral cavity and into the pouch to inject and/or withdraw inflation medium using an inflation/deflation needle 88 insertable into an inflation port in the region 82. The region 82 may be an integral portion of the pouch 80, or it may take the form of an inflatable ring 82*a* as shown on the pouch 80*a* of the eighth embodiment, which is shown in FIGS. 11A and 11B. FIG. 11A shows the ring undergoing expansion, while FIG. 11B shows the ring sufficiently expanded to open (optional) pleats 89 in the pouch 80*a*.

Pouch 90 of the ninth embodiment (FIG. 12) includes a pair of annular inflation chambers 92, 94 joined by a bi-directional valve 96 such that inflation medium displaced from one chamber passes through valve 96 into the other chamber. If it is desired to increase the diameter of distal orifice 98, a dilation tool (such as tool 36 of FIG. 4A) is positioned within the orifice 98 and expanded, causing inflation medium in the chamber 94 to pass through valve 96 and into chamber 92—thereby allowing ingested food to flow more freely through orifice 98. To decrease the diameter of distal orifice 98, the dilation tool is dilated against the upper chamber 92, to cause displacement of inflation medium into the lower chamber 94 and thereby to cause chamber 94 to expand radially inwardly to decrease the diameter of orifice 98.

Tenth Embodiment

Figure 13:
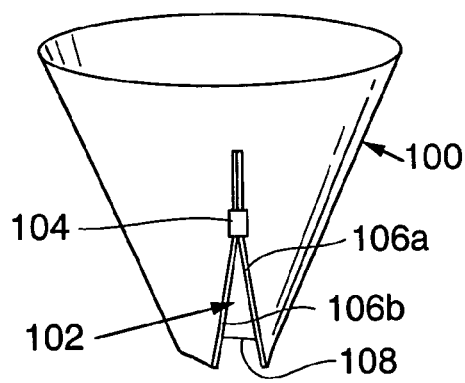
FIG. 13 is a perspective view of a tenth embodiment of a satiation device.

Pouch 100 of the tenth embodiment (FIG. 13) uses a zipper configuration (similar to that found on plastic storage bags) to increase or decrease the size of the distal orifice. A longitudinal cut 102 is provided in the pouch wall. A zipper carriage 104 is slidable in a proximal direction along the cut to separate the edges 106*a*, 106*b* and to thus increase the size of the distal orifice 108. Movement of the carriage 104 in the distal direction joins the edges 106*a*, 106*b* together to decrease the size of the distal orifice 108.

Eleventh Embodiment

Figure 14A:
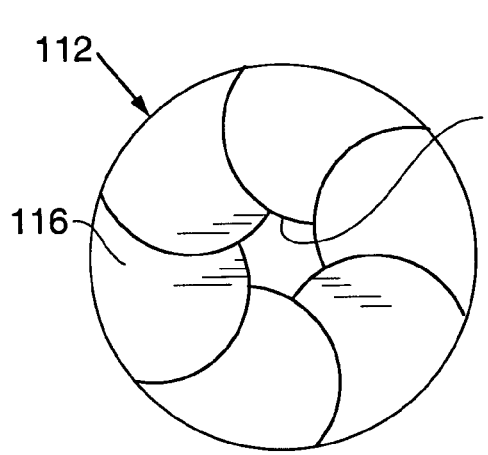
FIGS. 14A and 14B are bottom elevation views of an eleventh embodiment of a satiation device, showing the distal orifice in a reduced-diameter configuration and in an expanded-diameter configuration, respectively.
Figure 14B:
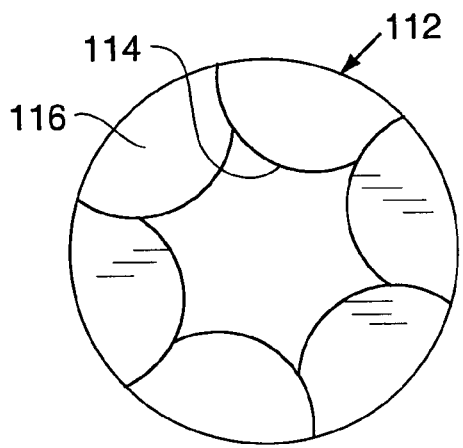
Figure 15A:
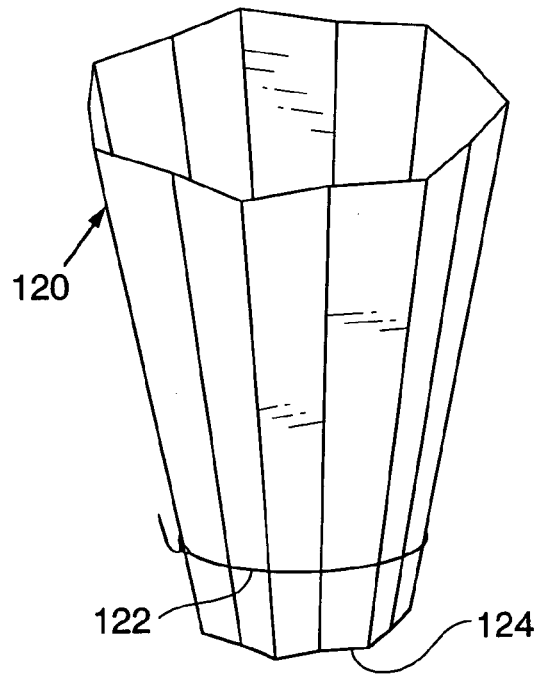
FIGS. 15A and 15B are perspective views of twelfth embodiment of a satiation device.
Figure 15B:
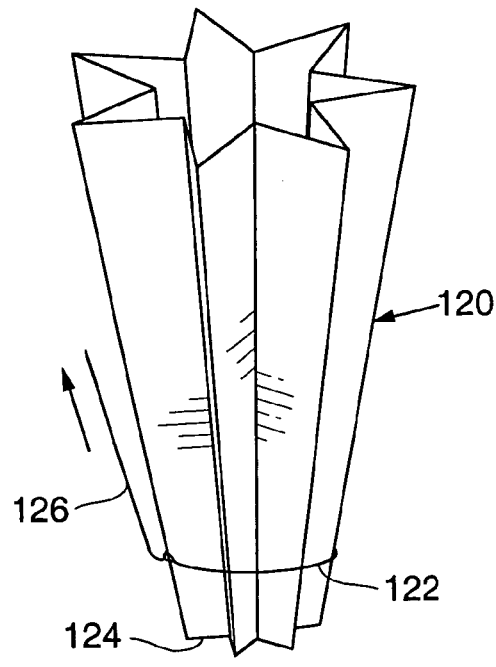

FIGS. 14A and 14B show the distal end of an eleventh embodiment of a pouch 110. The distal end of pouch 110 includes a diaphragm 112 defining distal orifice 114. The diaphragm 112 is similar to the shutter of a camera in the sense that it includes leaves 116 that are rotatable to increase or decrease the distal orifice 114, depending on the direction of rotation. Various mechanisms may be used for rotating the diaphragm, including a manual screw-type actuator engageable by an endoscopic tool passed through the oral cavity and into the pouch, or a microelectromechanical motor activated from an endoscope accessory under direct visualization or activated wirelessly from outside of the patient's body.

Twelfth Embodiment

In accordance with a twelfth embodiment of a pouch 120, the pouch 120 includes a drawstring 122 surrounding the distal portion of the pouch. The string may be held in position by feeding it through a sleeve (such as is the case with drawstring pants) or through spaced apart belt-loop type loops. The size of the distal orifice 124 is reduced by pulling on the free end 126 of the drawstring, causing it to cinch the pouch 120.

Cutting Tools

Another technique that may be used to increase the size of the distal orifice of a satiation pouch is to use a cutting tool to cut a larger opening into the pouch. If performed on a pouch located within the body, the tool is an endoscopic tool that is introduced through the esophagus and into pouch, preferably under visualization.

If the pouch is tapered towards its distal end, removing a section of the distal end will increase the orifice size. FIGS. 16 through 19B show tools that may be used for this purpose.

Figure 16:
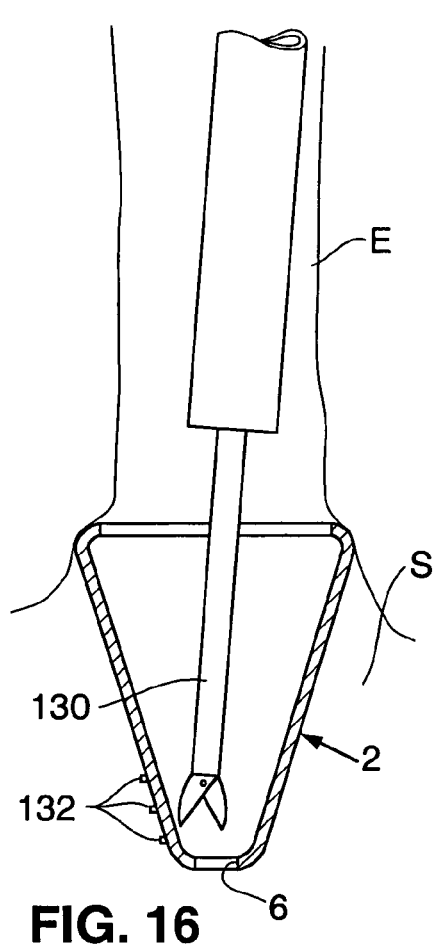
FIGS. 16 through 18 are side perspective views showing the distal orifice of a satiation pouch being expanded using a variety of cutting tools.

FIG. 16 shows pouch 2 positioned within a stomach S. Endoscopic scissors 130 are passed through the esophagus and into the pouch 2, and are used to trim the distal end off of the pouch 2, thereby increasing the size of distal orifice 6. In any of the cutting tool embodiments, the pouch 2 may include markings 132 which indicate where cuts should be formed to achieve various orifice diameters.

Figure 17:
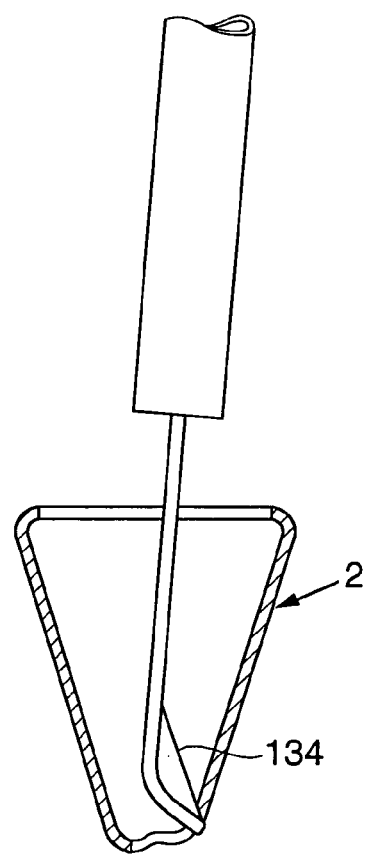
Figure 18:
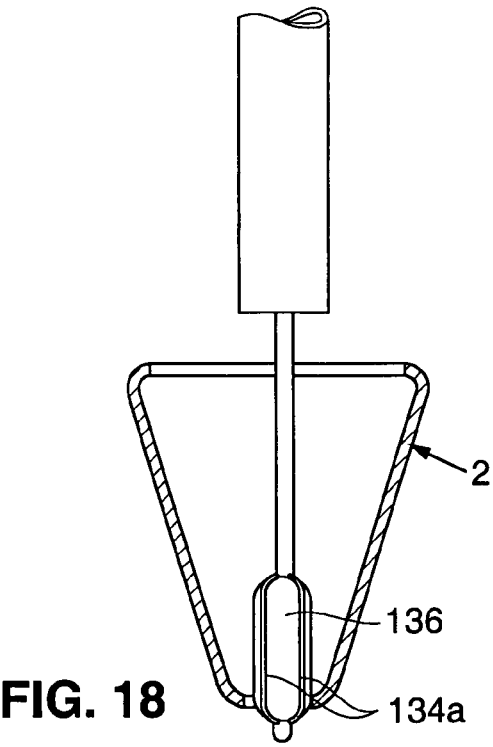

Referring to FIG. 17, the distal end of the pouch 2 may be opened using an endoscopic electrode, such as a bi-polar or monopolar RF electrode wire 134 that may be energized and drawn across the pouch material to remove a portion of the pouch 2. A variety of electrode configurations may be used, including the "bow" configuration shown, a wire having a distal tip electrode, or a plurality of wires 134a configured in a basket-type arrangement as shown in FIG. 18. Such a basket-type arrangement may be expanded into contact with the pouch using a balloon 136. Alternatively, the wires may be shape-memory wires pre-formed to the expanded positioned and contained within a sheath until they are positioned within the pouch, and then released into their expanded position to perform the cutting operation.

Other forms of cutting-type tools may also be used to increase the distal orifice size on a satiation pouch. For example, the pouch may be incised with a laser directed onto the wall of the pouch, or using a jet of a chemical substance selected to dissolve a portion of the pouch but to also be well-tolerated by the gastric mucosa and the patient. In one embodiment, the pouch may be made of a material that is not affected by the chemical, with a distal cuff on the pouch that is readily dissolved by the chemical. Chemical is then directed on the cuff if it becomes necessary to increase the orifice size.

As yet another example, a cutting device similar to an aortic-punch used for cardio-vascular applications may be used to enlarge the distal orifice of a satiation pouch. Referring to FIGS. 19A and 19B, punch device 138 includes a hollow elongate shaft 140 fluidly coupled to a suction port 142. A rod 144 extends through the shaft 140 and a punch tip 146 is carried by the rod 144. Sharp cutting edges 148 are formed along the proximal perimeter of the punch tip 146. An actuator 150 coupled to the rod 144 moves the punch tip 146 towards and away from the end of the shaft 140.

During use, the instrument is passed through the pouch such that the punch tip 146 extends out the distal orifice of the pouch. The shaft 140 is moved laterally to cause a portion of the pouch surrounding the distal orifice to be captured between the punch tip 146 and the perimeter of the shaft 140. The user manipulates the actuator 150 to draw the punch tip 146 in a proximal direction, causing the cutting edges 148 to slice through the captured portion of the pouch. Suction applied to the suction port 142 removes the removed fragments of the pouch from the operative site. The process is repeated until the distal orifice has been increased to the desired size.

It should be noted that, although these tools describe use of cutting tools to cut along the circumference of the pouch, a pouch might have its distal orifice size increased by simply forming a longitudinal cut adjacent to its distal end.

Various embodiments of satiation devices and methods for expanding exit orifices have been described herein. These embodiments are given by way of example and are not intended to limit the scope of the present invention. It should be appreciated, moreover, that the various features of the embodiments that have been described may be combined in various ways to produce numerous additional embodiments. Also, while various materials, dimensions, shapes, implantation locations, etc. have been described for use with disclosed embodiments, others besides those disclosed may be utilized without exceeding the scope of the invention. Lastly, while the pouches have been described for use in controlling feelings of hunger, the barrier devices described herein may be equally suitable for use with other prosthetic devices positionable within the body, including prosthetic valves implanted in the lower esophagus or proximal stomach for controlling gastro-esophageal reflux disease (GERD).

What is claimed is:

1. A method of treating obesity, comprising the steps of:
    providing a base device and a prosthetic device;
    coupling the base device to tissue at the gastro-esophageal junction region of the patient;
    with the base device coupled to the tissue, positioning the prosthetic device in contact with the base device, the prosthetic device selected to form a restriction slowing passage of food from the esophagus into the stomach; and
    monitoring a weight loss rate of the patient over a period of time, and, if it is determined that the weight loss rate is faster or slower than a desired weight loss rate, modifying the restriction to increase or decrease the weight loss rate.

2. The method of claim 1, wherein the modifying step is performed after the step of positioning the prosthetic device in contact with the base device.

3. The method of claim 1, wherein:
    prior to the modifying step food ingested by the patient flows into the stomach at a first rate; and
    following the modifying step food ingested by the patient flows into the stomach at a second rate different than the first rate.

4. The method of claim 3, wherein the first rate is faster than the second rate.

5. The method of claim 3, wherein the first rate is slower than the second rate.

6. The method of claim 1, wherein the modifying step includes altering the prosthetic device to modify the size of the restriction.

7. The method of claim 1, wherein the positioning step couples the prosthetic device to the base device.

8. The method of claim 1, wherein the base device includes an annular ring, and wherein the positioning includes coupling the prosthetic device to the annular ring.

9. The method of claim 1, wherein positioning the prosthetic device in contact with the base device includes causing the base device to retain the prosthetic device in the gastroesophageal junction region.

10. The method of claim 1, wherein positioning the prosthetic device in contact with the base device includes coupling the prosthetic device to the base device.

* * * * *

UNITED STATES PATENT AND TRADEMARK OFFICE
CERTIFICATE OF CORRECTION

| | | |
|---|---|---|
| PATENT NO. | : 7,628,821 B2 | Page 1 of 1 |
| APPLICATION NO. | : 11/195204 | |
| DATED | : December 8, 2009 | |
| INVENTOR(S) | : Stack et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 204 days.

Signed and Sealed this

Twenty-first Day of December, 2010

David J. Kappos
*Director of the United States Patent and Trademark Office*